(12) United States Patent
Ginn et al.

(10) Patent No.: US 6,719,777 B2
(45) Date of Patent: *Apr. 13, 2004

(54) CLOSURE DEVICE AND METHODS FOR MAKING AND USING THEM

(75) Inventors: Richard S. Ginn, San Jose, CA (US); William N. Aldrich, Los Altos, CA (US); W. Martin Belef, San Jose, CA (US); Steven N. Roe, San Mateo, CA (US)

(73) Assignee: Integrated Vascular Systems, Inc., Sunnyvale, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 92 days.

(21) Appl. No.: 09/732,178

(22) Filed: Dec. 7, 2000

(65) Prior Publication Data

US 2002/0082641 A1 Jun. 27, 2002

(51) Int. Cl.⁷ .............................................. A61B 17/08
(52) U.S. Cl. ...................................................... 606/213
(58) Field of Search ................................ 606/213, 221, 606/151, 153, 155, 154, 72, 75, 76; 411/531, 533

(56) References Cited

U.S. PATENT DOCUMENTS

| | | |
|---|---|---|
| 3,604,425 A | 9/1971 | LeRoy |
| 3,757,629 A | 9/1973 | Schneider |
| 3,805,337 A | 4/1974 | Branstetter |
| 4,217,902 A | 8/1980 | March |
| 4,396,139 A | 8/1983 | Hall et al. |
| 4,485,816 A | 12/1984 | Krumme |
| 4,505,274 A | 3/1985 | Speelman |
| 4,586,503 A | 5/1986 | Kirsch et al. |
| 4,777,950 A | 10/1988 | Kees, Jr. |
| 4,860,746 A | 8/1989 | Yoon |

(List continued on next page.)

FOREIGN PATENT DOCUMENTS

| | | | |
|---|---|---|---|
| WO | 99/62408 | * 9/1999 | ........... A61B/17/08 |
| WO | WO 00/56223 | 9/2000 | |
| WO | WO 00/56227 | 9/2000 | |

OTHER PUBLICATIONS

PCT Publication No. WO 00/07640, "Vascular Suction Cannula, Dialator and Surgical Stapler", Steven Tallarida, et al., Feb. 17, 2000.
PCT Publication No. WO 98/24374, "Vascular Wound Closure System", Yong Zhu, et al., Jun. 11, 1998.
PCT Publication No. WO 97/20505, "Vascular Wound Closure Device", Yong Zhu, et al., Jun. 12, 1997.

*Primary Examiner*—Michael J. Milano
*Assistant Examiner*—D. Jacob Davis
(74) *Attorney, Agent, or Firm*—Orrick, Herrington & Sutcliffe LLP

(57) ABSTRACT

A vascular clip includes a peripheral body defining a plane, and tines extending from the body transversely with respect to the plane, the tines biased towards a planar configuration. The clip includes expandable elements disposed along its periphery that are biased to expand from compressed to expanded states for increasing a diameter of the clip upon deployment. The clip is provided within a housing slidably mounted on an introducer sheath. The sheath is introduced through a puncture into a blood vessel, and after a procedure is performed via the sheath, the housing is advanced into the puncture and the clip deployed until the tines engage tissue adjacent the opening in the vessel wall. The sheath is withdrawn from the patient, leaving the clip in place. The tines at least partially move towards the planar configuration to pull the engaged tissue together and close the opening.

16 Claims, 5 Drawing Sheets

U.S. PATENT DOCUMENTS

| | | |
|---|---|---|
| 4,865,026 A | 9/1989 | Barrett |
| 4,917,087 A | 4/1990 | Walsh et al. |
| 4,950,258 A | 8/1990 | Kawai et al. |
| 5,007,921 A | 4/1991 | Brown |
| 5,026,390 A | 6/1991 | Brown |
| 5,053,008 A | 10/1991 | Bajaj |
| 5,108,420 A | 4/1992 | Marks |
| 5,156,609 A | 10/1992 | Nakao et al. |
| 5,176,648 A | 1/1993 | Holmes et al. |
| 5,192,302 A | 3/1993 | Kensey et al. |
| 5,222,974 A | 6/1993 | Kensey et al. |
| 5,304,184 A | 4/1994 | Hathaway et al. |
| 5,334,217 A * | 8/1994 | Das ............................ 606/213 |
| 5,366,458 A | 11/1994 | Korthoff et al. |
| 5,478,354 A | 12/1995 | Tovey et al. |
| 5,527,322 A | 6/1996 | Klein et al. |
| 5,674,231 A | 10/1997 | Green et al. |
| 5,683,405 A | 11/1997 | Yacoubian et al. |
| 5,695,505 A | 12/1997 | Yoon |
| 5,782,844 A | 7/1998 | Yoon et al. |
| 5,782,861 A | 7/1998 | Cragg et al. |
| 5,810,846 A | 9/1998 | Virnich et al. |
| 5,810,851 A | 9/1998 | Yoon |
| 5,830,125 A | 11/1998 | Scribner et al. |
| 5,879,366 A | 3/1999 | Shaw et al. |
| 5,910,155 A | 6/1999 | Ratcliff et al. |
| 5,984,934 A | 11/1999 | Ashby et al. |
| 6,007,563 A | 12/1999 | Nash et al. |
| 6,036,720 A | 3/2000 | Abrams et al. |
| 6,077,281 A | 6/2000 | Das |
| 6,077,291 A | 6/2000 | Das |
| 6,080,182 A | 6/2000 | Shaw et al. |
| 6,080,183 A | 6/2000 | Tsugita et al. |
| 6,113,612 A | 9/2000 | Swanson et al. |
| 6,152,937 A | 11/2000 | Peterson et al. |
| 6,402,765 B1 * | 6/2002 | Monassevitch et al. ..... 606/151 |
| 2001/0047180 A1 * | 11/2001 | Grudem et al. ............. 606/153 |

* cited by examiner

CLOSURE DEVICE AND METHODS FOR MAKING AND USING THEM

FIELD OF THE INVENTION

The present invention relates generally to apparatus and methods for engaging tissue and/or closing openings through tissue, e.g., into body lumens, and more particularly to devices for closing a puncture in a blood vessel or other body lumen formed during a diagnostic or therapeutic procedure, and to methods for making and using such devices.

BACKGROUND

Catheterization and interventional procedures, such as angioplasty or stenting, generally are performed by inserting a hollow needle through a patient's skin and intervening tissue into the vascular system. A guide wire may then be passed through the needle lumen into the patient's blood vessel accessed by the needle. The needle may be removed, and an introducer sheath may be advanced over the guide wire into the vessel, e.g., in conjunction with or subsequent to a dilator. A catheter or other device may then be advanced through a lumen of the introducer sheath and over the guide wire into a position for performing a medical procedure. Thus, the introducer sheath may facilitate introduction of various devices into the vessel, while minimizing trauma to the vessel wall and/or minimizing blood loss during a procedure.

Upon completion of the procedure, the devices and introducer sheath may be removed, leaving a puncture site in the vessel wall. External pressure may be applied to the puncture site until clotting and wound sealing occur. This procedure, however, may be time consuming and expensive, requiring as much as an hour of a physician's or nurse's time. It is also uncomfortable for the patient, and requires that the patient remain immobilized in the operating room, catheter lab, or holding area. In addition, a risk of hematoma exists from bleeding before hemostasis occurs.

Various apparatus have been suggested for percutaneously sealing a vascular puncture by occluding the puncture site. For example, U.S. Pat. Nos. 5,192,302 and 5,222,974, issued to Kensey et al., describe the use of a biodegradable plug that may be delivered through an introducer sheath into a puncture site. When deployed, the plug may seal the vessel and provide hemostasis. Such devices, however, may be difficult to position properly with respect to the vessel, which may be particularly significant since it is generally undesirable to expose the plug material, e.g., collagen, within the bloodstream, where it may float downstream and risk causing an embolism.

Another technique has been suggested that involves percutaneously suturing the puncture site, such as that disclosed in U.S. Pat. No. 5,304,184, issued to Hathaway et al. Percutaneous suturing devices, however, may require significant skill by the user, and may be mechanically complex and expensive to manufacture.

U.S. Pat. No. 5,478,354, issued to Tovey et al., discloses a surgical fastener including an annular base having legs that, in a relaxed state, extend in a direction substantially perpendicular to a plane defined by the base and slightly inwards toward one another. During use, the fastener is fit around the outside of a cannula, thereby deflecting the legs outward. The cannula is placed in an incision, and the fastener is slid along the cannula until the legs pierce into skin tissue. When the cannula is withdrawn, the legs move towards one another back to the relaxed state to close the incision.

U.S. Pat. Nos. 5,007,921 and 5,026,390, issued to Brown, disclose staples that may be used to close a wound or incision. In one embodiment, an "S" shaped staple is disclosed that includes barbs that may be engaged into tissue on either side of the wound. In another embodiment, a ring-shaped staple is disclosed that includes barbs that project from the ring. Sides of the ring may be squeezed to separate the barbs further, and the barbs may be engaged into tissue on either side of a wound. The sides may then be released, causing the barbs to return closer together, and thereby pulling the tissue closed over the wound. These staples, however, have a large cross-sectional profile and therefore may not be easy to deliver through a percutaneous site to close an opening in a vessel wall.

Accordingly, devices for engaging tissue, e.g., to close a vascular puncture site, would be considered useful.

SUMMARY OF THE INVENTION

The present invention is directed to devices and methods for engaging tissue, e.g., to connect tissue segments together or to close and/or seal openings through tissue, such as in a wall of a body lumen. More particularly, the present invention is directed to vascular closure devices or clips for closing a puncture in a wall of a blood vessel formed during a diagnostic or therapeutic procedure, and to methods for making and using such devices.

In accordance with one aspect of the present invention, a device for closing an opening in a body lumen is provided that includes a generally annular-shaped body defining a plane, and a plurality of tissue engaging portions extending from the annular-shaped body substantially transversely with respect to the plane. In this embodiment, opposing tissue engaging portions, e.g., tines, are biased towards a substantially planar configuration lying in the plane. In one embodiment, the tissue engaging portions are biased towards one another, e.g., to close a puncture site or other opening through tissue. Alternatively, the tissue engaging portions may be biased away from one another.

In a preferred embodiment, the tissue engaging portions are integrally formed with the annular-shaped body, e.g., from a sheet of material, such as Nitinol or other superelastic alloy. The tissue engaging portions may be formed with the sheet of material in the substantially planar configuration. The tissue engaging portions may be deflected substantially transversely with respect to the plane to define a substantially transverse configuration. Alternatively, the device may be formed from an elongate wire or tube that may be wound to form an enclosed body.

In one embodiment, the tissue engaging portions, e.g., tines, optionally including barbs, for penetrating tissue, may be disposed substantially symmetrically about a central axis. Alternatively, the tissue engaging portions may be disposed in opposing sets along a linear axis.

In accordance with another aspect of the present invention, a device for engaging tissue, e.g., to close an opening in a body lumen, is provided that includes a generally annular-shaped body defining a plane. A plurality of tissue engaging portions extend from the annular-shaped body substantially transversely with respect to the plane. In a preferred embodiment, opposing tissue engaging portions of the device are biased towards a substantially planar configuration lying in the plane, as described above.

One or more expandable elements are disposed along a periphery of the annular-shaped body. The expandable elements are expandable between expanded and compressed states for increasing and reducing a peripheral dimension of the annular-shaped body, respectively. In one embodiment, the expandable elements may be an enclosed cell, e.g. a diamond-shaped cell, having a first width in the expanded state and a second width in the compressed state that is smaller than the first width. Alternatively, the expandable elements may be a zig-zag element or an arcuate element. Preferably, the expandable elements are biased to the expanded state, e.g., by appropriate heat treating of the expandable elements. Alternatively, the expandable elements may be biased to the compressed state.

In accordance with yet another aspect of the present invention, a clip, such as those described above, may be loaded on a delivery apparatus and used to close and/or seal an opening in a wall of a body lumen. The apparatus generally includes a sheath including proximal and distal ends defining a longitudinal axis therebetween. A housing is slidably disposed on the sheath, the housing including an annular cavity therein. A clip, such as those described above, is disposed within the cavity with the tissue engaging portions disposed substantially distally.

The housing is preferably actuable for advancing the clip distally towards the distal end of the sheath, e.g., to deploy the clip from the cavity. For example, the apparatus may include an actuator coupled to the housing, the actuator configured for advancing the housing distally to deploy the clip. Preferably, the actuator includes a spring mechanism for biasing the housing distally upon activation of the actuator. In addition, the apparatus may include a locator element for positioning the distal end of the sheath, such as a bleed back lumen or a mechanical locator.

During use, the distal end of the sheath, with the housing and clip near its proximal end, may be positioned through a patient's skin along a passage and into a body lumen via an opening in the wall of the body lumen. One or more instruments may be introduced through the lumen of the sheath into the body lumen. A diagnostic or therapeutic procedure may be performed using the instruments at a location accessed via the body lumen. For example, in a preferred method, the body lumen is a peripheral blood vessel, such as a femoral artery, and the procedure may include angioplasty, atherectomy, stent delivery, delivery of a therapeutic agent, and/or tissue ablation.

The sheath may be manipulated, for example, with the aid of a locator element, to position the distal end with respect to the opening, e.g., to ensure that the clip engages a wall of the body lumen or other tissue proximal to the opening and is not advanced into the body lumen itself. The housing is advanced distally into the passage, e.g., until the tissue engaging portions of the clip substantially engage the wall of the body lumen or other tissue proximal to the opening in the wall of the body lumen. In addition, or alternatively, the clip may be deployed from the housing, for example, by an ejector within the housing. The sheath may then be withdrawn from the body lumen and passage, leaving the clip in the passage. As the distal end of the sheath is withdrawn through the clip, the tissue engaging portions automatically at least partially move towards the planar configuration to pull the engaged tissue together and substantially close the opening.

In one embodiment, the clip automatically expands to an enlarged cross-section when the clip is deployed from the housing. Thus, the clip may be compressed to facilitate loading into the housing, and thereby provide a reduced profile for the clip. This may be useful to allow the clip to be delivered through a smaller puncture.

A method according to the present invention may include causing a clip or other closure element to engage tissue, e.g., muscle, fat, fascia, and the like, that is proximal to the body lumen. Thus, unlike previously known methods, which are directed to closing the wall of a blood vessel using clips or sutures, the present invention may include deploying a closure element in the passage to cause it to engage intermediate tissue between the patient's skin and the wall of the body lumen. When performed in this manner, the need to precisely position a closure element may be avoided as is required when engaging the wall of a vessel. Instead, the closure element may be located and delivered at a range of locations along the length of the passage yet still close and/or seal the passage. In effect, extra-vascular tissue is engaged to close the passage and thereby cause sealing of the wound. When the closure element is deployed, it is preferably planar, e.g., extending substantially parallel to the surface of the patient's skin, although not necessarily so.

Other objects and features of the present invention will become apparent from consideration of the following description taken in conjunction with the accompanying drawings.

DETAILED DESCRIPTION OF THE PREFERRED EMBODIMENTS

Figure 1A:
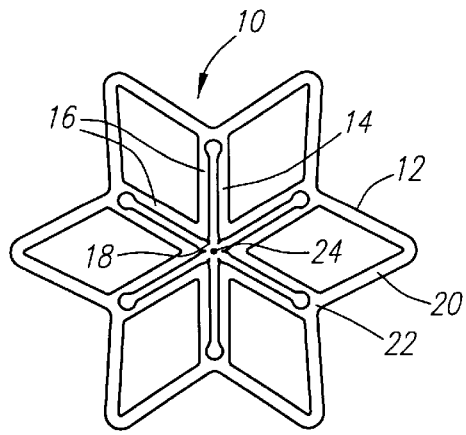
FIG. 1A is a top view of a first embodiment of a clip including a plurality of tissue engaging portions in a planar orientation, in accordance with the present invention.

Turning now to the drawings, FIGS. 1A–1D show a first preferred embodiment of a closure device or clip 10 for closing an incision, puncture, or other passage communicating with a blood vessel or other body lumen (not shown). The clip 10 includes a peripheral body 12 and a plurality of tissue engaging portions 14. Each tissue engaging portion 14 includes a pair of legs 16 terminating in a tine 18 configured for penetrating or otherwise engaging tissue. The tines 18 may include a variety of known pointed tips, such as a bayonet tip, and/or may include barbs (not shown) along an edge or planar surface of the tine 28. The tissue engaging portions 14 are disposed substantially symmetrically about a central axis 24. The body 12 also preferably includes a plurality of expandable cells 20 that are connected by hinged regions 22 that also connect adjacent tissue engaging portions 14.

In a preferred embodiment, the body 12 and tissue engaging portions 14 are integrally formed from a single sheet of material, preferably a superelastic alloy, such as a nickel-titanium ("Nitinol") alloy. Portions of the sheet may be removed using conventional methods, such as laser cutting, chemical etching, and the like, to form the clip 10. FIG. 1A shows the clip 10 with the tissue engaging portions 14 in a substantially planar configuration lying in a plane defined by the sheet. The clip 10 may include one or more radiopaque markers or other markers visible using external imaging, such as fluoroscopy. For example, the entire clip 10 may be coated with radiopaque material, or one or more discrete markers may be provided at predetermined locations on the clip 10.

Figure 1B:
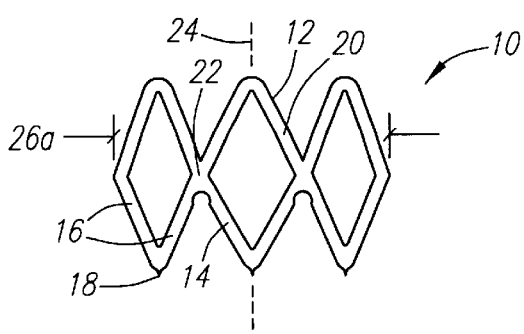
FIGS. 1B and 1C are side views of the clip of FIG. 1, with the tissue engaging portions oriented substantially transversely from the planar orientation, in reduced and expanded diameters, respectively.
Figure 1C:
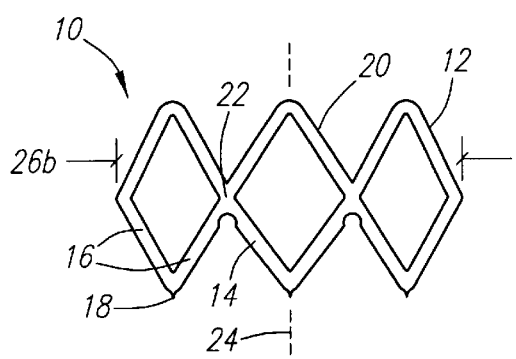
Figure 1D:
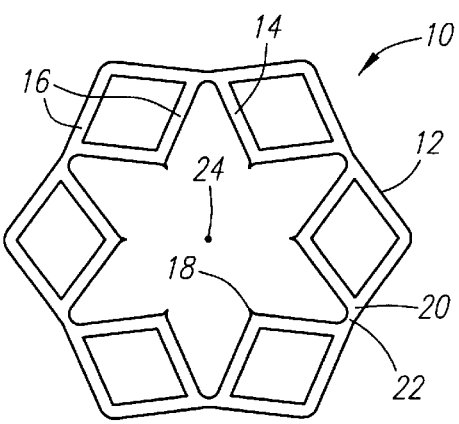
FIG. 1D is a top view of the clip of FIG. 1 with the tines oriented substantially transversely from the planar orientation.

As shown in FIGS. 1B and 1D, the tissue engaging portions 14 may be deflected such that they extend from the body 12 substantially transversely with respect the plane defined by the sheet. Preferably, the tissue engaging portions 14 are oriented substantially parallel to the axis 24 to define a transverse configuration, as shown in FIG. 1B. Alternatively, the tissue engaging portions 14 may define an angle with respect to the axis 24, as shown in FIG. 1D. In the clip's transverse configuration, the body 12 has a generally annular shape, e.g., a hexagonal shape as shown in FIG. 1D. Preferably, the body 12 is sufficiently flexible such that the clip 10 assumes a generally circular or elliptical shape (not shown), e.g., conforming to an exterior surface of a delivery device (not shown) used to delivery the clip 10.

Preferably, the tissue engaging portions 14 are biased from the transverse configuration towards one another, i.e., towards the planar configuration of FIG. 1A. Thus, with the tissue engaging portions 14 in the transverse configuration, the tines 18 may be engaged with tissue, e.g. adjacent to a puncture site. When the clip 10 is released, the tissue engage portions 14 may attempt to return to the planar configuration, thereby drawing the engaged tissue together and substantially closing and/or sealing the puncture site.

In addition, the expandable cells 20 may be expandable from a compressed state, shown in FIG. 1B, to an expanded state, shown in FIG. 1C. Preferably, the expandable cells 20 are biased to the expanded state, but may be compressed to the compressed state, e.g., by constraining the clip 10. In one embodiment, the clip 10 is formed with the expandable cells 20 in the expanded state. With the clip in its transverse configuration, the expandable cells 20 may be circumferentially and/or radially compressed to the compressed state such that the clip 10 defines a first diameter 26a, shown in FIG. 1B. The clip 10 may be constrained at the first diameter, e.g., by loading the clip 10 into a delivery device (not shown), as described further below. When released from the constraint, e.g., when deployed from the delivery device, the clip 10 may automatically expand to a second diameter 26b, shown in FIG. 1C. Thus, the expandable cells 20 may reduce the profile of the clip 10 during delivery, e.g., to facilitate introduction of the clip 10 through a smaller puncture or other passage.

In an alternative embodiment, the clip 10 may be formed from a shape memory alloy, e.g., Nitinol, with the expandable cells in the compressed state. With the clip 10 in the transverse configuration, the clip 10 may be expanded, e.g., by applying a force radially outwards against an inner surface of the clip 10, thereby expanding the expandable cells 20 to the expanded state and expanding the clip 10 to the second diameter 26b. The expandable cells 20 may then be heat treated to cause the expandable cells 20 to "remember" the expanded state, as is known to those skilled in the art. It may also be necessary to subsequently heat treat the clip 10 further, e.g. with the tissue engaging portions 14 in the planar configuration to cause the tissue engaging portions 14 to "remember" and be biased to the planar configuration, as is known to those skilled in the art.

Figure 2:
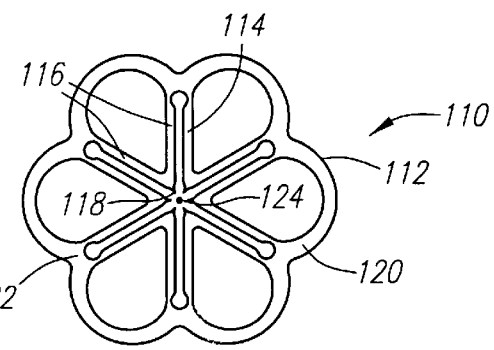
FIG. 2 is a top view of a second embodiment of a clip, in accordance with the present invention.

Turning to FIG. 2, a second preferred embodiment of a clip 110 is shown that includes a peripheral body 112 and a plurality of tissue engaging portions 114. Each tissue engaging portion 114 includes a pair of legs 116 terminating in a tine 118. The tissue engaging portions 114 are disposed substantially symmetrically about a central axis 124. The body 112 also preferably includes a plurality of expandable cells 120 that are connected by hinged regions 122 that also connect adjacent tissue engaging portions 114, similar to the first embodiment described above.

The tissue engaging portions 114 may be deflected such that they extend substantially transversely from the body 112 (not shown). Preferably, the tissue engaging portions 114 may be oriented substantially parallel to the axis 124 to define a transverse configuration such that the body 112 has a generally annular shape. The tissue engaging portions 114 are preferably biased from the transverse configuration towards one another, i.e., towards the planar configuration of FIG. 2, similar to the previous embodiment.

The expandable cells 120 have a generally arcuate shape that may be expandable from a first width to a second wider width (not shown), behaving similarly to the diamond-shaped cells of the previous embodiment. Thus, the expandable cells 120 may be biased to the expanded state, but may be compressed to the compressed state, as described above.

Figure 3:
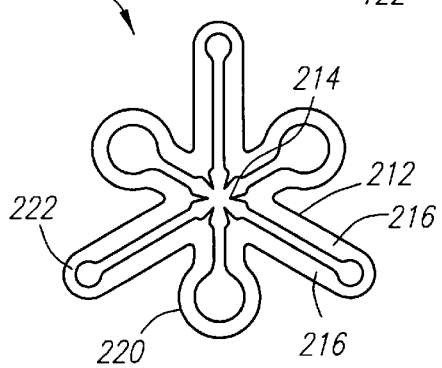
FIG. 3 is a top view of a third embodiment of a clip, in accordance with the present invention.

Turning to FIG. 3, another embodiment of a clip 210 is shown that includes a peripheral body 212 including a plurality of arms 216 extending between tissue engaging portions or tines 214; expandable cells 220, and hinged regions 222. The clip 210 is preferably formed from a single sheet of material, similar to the embodiments described above, with the tines 214 biased to a planar configuration, as shown. The body 212 is deflectable to a transverse configuration (not shown) such that the tines 212 are oriented substantially transversely with respect to the plane of the sheet. The body 212, and particularly the arms 216, are sufficiently flexible such that the clip 210 may assume a generally annular shape in the transverse configuration, e.g., to facilitate loading of the clip 210 onto a delivery device (not shown).

The expandable cells 220 are substantially enclosed loops that may at least partially open from a compressed state (shown in FIG. 2), to an expanded state (not shown). Preferably, the loops are biased to the expanded state, similar to the embodiments described above, thereby allowing the clip 210 to assume a reduced diameter and an expanded diameter.

Figure 4:
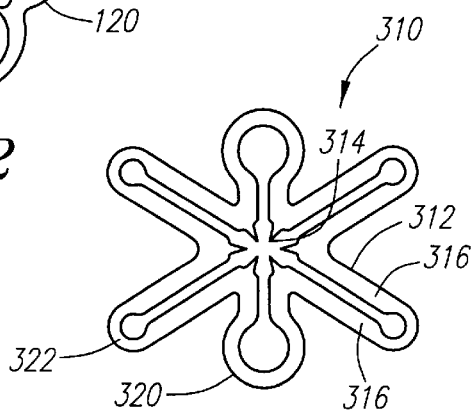
FIG. 4 is a top view of a fourth embodiment of a clip, in accordance with the present invention.

Turning to FIG. 4, a fourth preferred embodiment of a clip 310 is shown, that is similar to the embodiment shown in FIG. 3, except that the clip 310 includes only two expandable cells 320. The expandable cells 320 are still disposed in a substantially symmetrical arrangement to facilitate expansion of the clip 310 in a generally uniform manner. As will be appreciated by those skilled in the art, a clip in accordance with the present invention may have a variety of configurations, including two or more tissue engaging portions or tines, and including one or more expandable cells (or optionally no expandable cells). Preferably, the tissue engaging portions and/or expandable cells are arranged in a substantially symmetrical configuration, for example, about a central axis.

Figure 5:
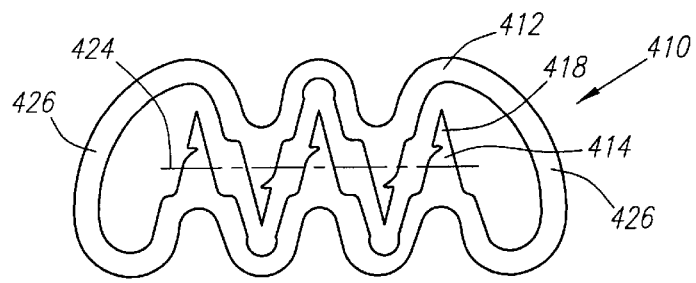
FIG. 5 is a top view of a fifth embodiment of a clip, in accordance with the present invention.

Turning to FIG. 5, a fifth preferred embodiment of a clip 410 is shown that includes a peripheral body 412 and a plurality of tissue engaging portions 414 terminating in tines 418. The clip 410 may be formed from a single sheet of material, such as Nitinol, similar to the embodiments described above.

Figure 6:
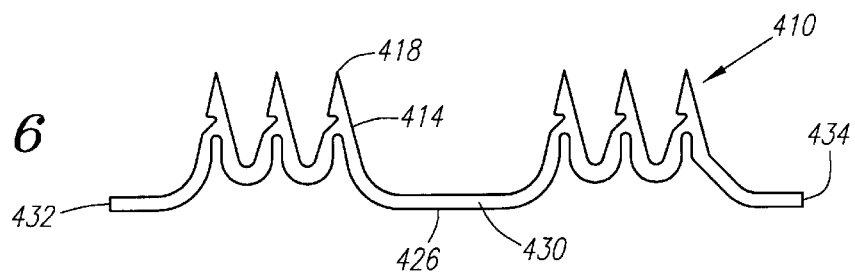
FIG. 6 is a top view of the clip of FIG. 5 with the clip unwound from its annular shape.

Alternatively, as shown in FIG. 6, the clip 410 may be formed from an elongate wire 430, e.g., a solid rod or hollow tube, such as a length of hypotube. Preferably, the tube 430 is semi-rigid or flexible, thereby accommodating deflection of the clip 410 between its planar and transverse configurations, as described further below. The tube 430 may be bent and tines 418 may be formed therein using conventional methods. Alternatively, tines 418 may be formed separately and attached to the tube 430, for example, by welding. The tube 430 may then be wound into an enclosed loop and the ends 432, 434 may be connected together, e.g., by welding, to provide a clip 410, such as that shown in FIG. 5.

In this embodiment, the tissue engaging regions 414 are disposed in opposing sets along an axis of symmetry 424 extending between looped regions 426, defining a substantially planar configuration. The tissue engaging portions 414 may be directed substantially transversely with respect to a plane defined by the planar configuration, but are preferably biased to return towards the planar configuration, similar to the embodiments described above.

Figure 7A:
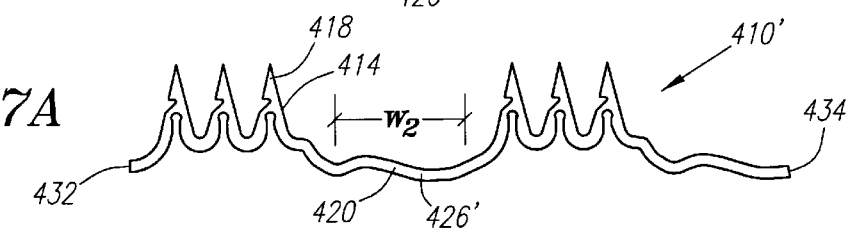
FIGS. 7A and 7B are top views of an alternative embodiment of the clip of FIG. 5, the clip shown unwound and including expandable elements shown in their expanded and compressed states, respectively.
Figure 7B:
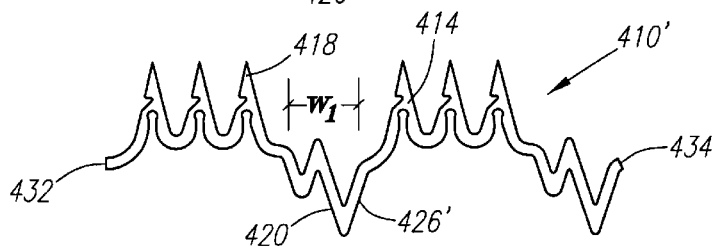
Figure 8A:
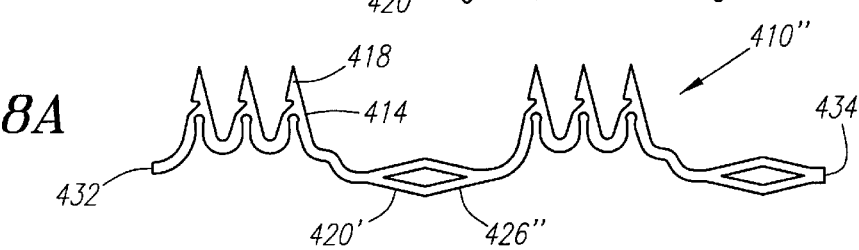
FIGS. 8A and 8B are top views of another alternative embodiment of the clip of FIG. 5, the clip shown unwound and including expandable cells shown in their expanded and compressed states, respectively.
Figure 8B:
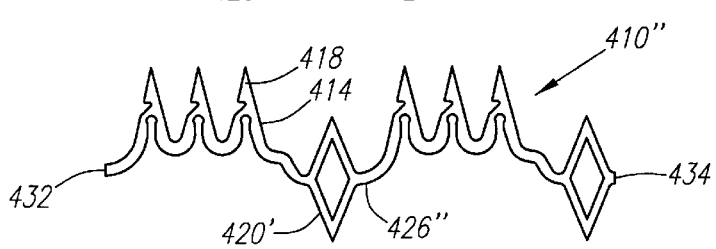

In an alternative embodiment, shown in FIGS. 7A and 7B, the regions 426' between the tissue engaging portions 414 include expandable elements 420, having a zig-zag shape, that are expandable between a compressed state and an expanded state. Thus, when the tube 412' is wound to form a clip (not shown), the zig-zag elements 420 are disposed at the looped regions 426' of the clip. The zig-zag elements 420 have a first width $w_1$ in the compressed state (FIG. 7B) and a second width $w_2$ in the expanded state that is larger than the first width (FIG. 7A). In a further alternative embodiment, shown in FIGS. 8A and 8B, the expandable elements are substantially enclosed cells 420', preferably having a diamond shape. Thus, similar to the embodiments described above, the expandable elements or cells allow the clip 410" to assume first and second diameters.

Figure 9:
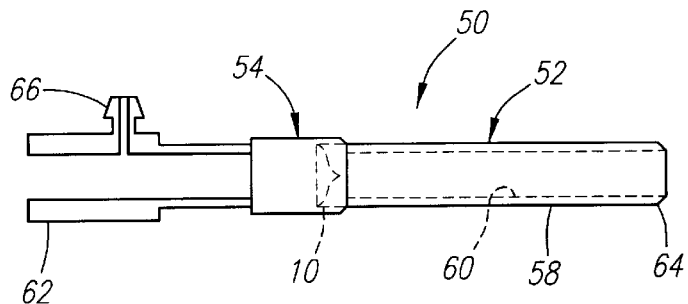
FIG. 9 is a side view of an apparatus for delivering a clip, including an introducer sheath and an actuator assembly, in accordance with the present invention.

Turning to FIG. 9, an apparatus 50 is shown that may be used to deliver a clip, such as any of the embodiments described above. Generally, the apparatus 50 includes an introducer sheath 52, and a housing 54 slidably disposed on the sheath 56. The sheath 52 includes a substantially flexible or semi-rigid tubular body 58 including a lumen 60 extending between its proximal and distal ends 62, 64. The distal end 64 has a size and shape to facilitate insertion into a blood vessel, e.g., having a tapered tip for facilitating substantially atraumatic introduction through the passage and at least partially into the vessel. The lumen 60 has a size for accommodating insertion of one or more devices therethrough, such as a catheter, guidewire, and the like (not shown). The sheath 52 also preferably includes a seal (not shown), such as a hemostatic valve, within the lumen 60 at or near the proximal end 62 that provides a fluid-tight seal, yet accommodates insertion of one or more devices into the lumen 60 without fluid passing proximally from the sheath 52.

Optionally, the sheath 52 may include a side port 66 that communicates with the lumen 60, for example, to allow the infusion of fluids into the lumen 60, through the sheath 52. Alternatively, or in addition, the side port 66 may be used to provide a "bleed back" indicator, such as that disclosed in co-pending application Ser. No. 09/680,837, filed Oct. 6, 2000, entitled "Apparatus and Methods for Positioning a Vascular Sheath," which is assigned to the assignee of the present invention. Alternatively, the apparatus 50 may include a mechanical locator (not shown), such as that disclosed in U.S. application Ser. No. 09/732,835, filed on the same day with the present application, entitled "Apparatus and Method for Delivering a Closure Device". The disclosure of these applications and any references cited therein are expressly incorporated herein.

The housing 54 is slidably disposed on an exterior of the sheath 52, the housing 54 configured for releasably holding the clip 10, e.g., within an annular cavity therein (not shown). The housing may be substantially permanently attached to the sheath 52 or, alternatively, the housing 54 may be attachable to the sheath 52, e.g., using an outer sleeve (not shown). This outer sleeve may have the housing thereon, and the sleeve may be advanced over the sheath 52, and coupled thereto at any time during its use. Exemplary embodiments of a housing for use with an apparatus in accordance with the present invention are disclosed in co-pending application Ser. Nos. 09/478,179, 09/546,998, and 09/610,238, the disclosures of which are expressly incorporated herein by reference.

The housing 54 is actuable from the proximal end 62 of the sheath 52, for example, by a housing actuator assembly (not shown), for advancing the clip 10 distally during deployment. A rod, cable, or other control wire (not shown) may couple the housing 54 to the actuator assembly. The housing actuator assembly may be detachable from the sheath 52, e.g., to facilitate introduction of devices into the lumen 60. In a preferred embodiment, the actuator may be biased to advance the housing 54 upon activation. Thus, when activated, the housing 54 may be advanced towards the distal end of the sheath 52 to deploy the clip 10.

Turning to FIGS. 10A–10D, the apparatus 50 may be used to deliver a clip 10, e.g., to close and/or seal an incision, puncture, or other passage 92 that extends from a patient's skin 94 through intervening tissue 96, and a wall 98 of the vessel 90. Alternatively, the apparatus 50 may be used to deliver any of the clips disclosed herein to engage tissue in other procedures, e.g., to connect tissue segments together or otherwise to secure tissue structures engaged by the clip with respect to one another. For example, the apparatus and clip may be used to attach an anastomosis during a bypass procedure. It will be appreciated by those skilled in the art that a clip and/or apparatus in accordance with the present application may be useful in a variety of procedures, including tubal ligations, and the like.

Generally, the clip 10 is pre-loaded in the housing 54 before the procedure. The clip 10 may be constrained in its substantially transverse configuration and then introduced over the distal end 64 of the sheath 52 and into the cavity or otherwise loaded in the housing 54. Because the tissue engaging portions (not shown) of the clip 10 are biased to a planar configuration, they may engage an inner wall (not shown) of the housing 54 or an outer surface of the sheath 52, thereby constraining the clip 10 in its transverse configuration. Alternatively, the clip 10 may be directed over the distal end 64 of the sheath 62, thereby causing the tissue engaging portions to deflect transversely from the planar configuration towards a substantially axial or distal configuration.

Figures 10A, 10B:
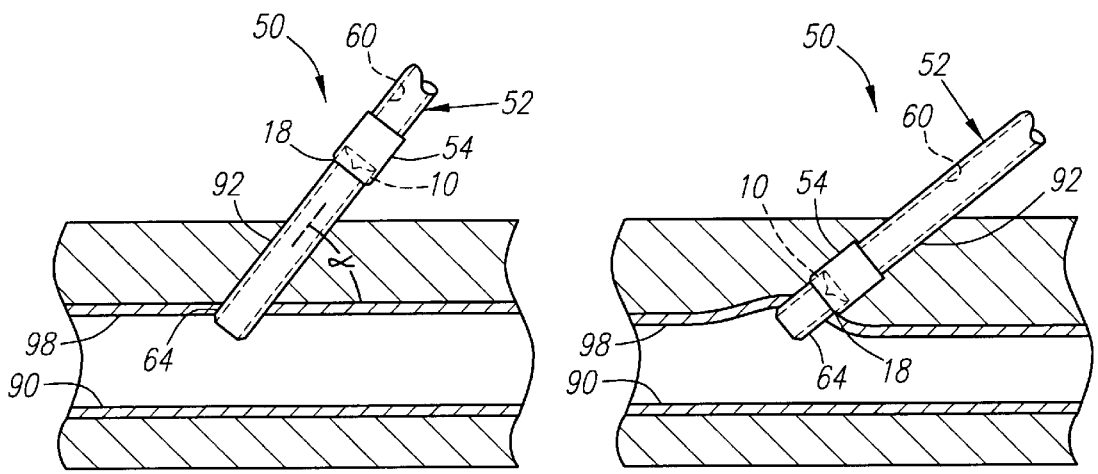
FIGS. 10A–10D are cross-sectional views of a blood vessel, showing a method for delivering a closure device into a passage communicating with the vessel such that the closure device engages the vessel wall.

As shown in FIG. 10A, the sheath 52 may be inserted or otherwise positioned within the blood vessel 90, i.e., through the passage 92. The sheath 52 is preferably provided with the housing 54 in its proximal position, e.g., without the housing actuator assembly (not shown) attached. Alternatively, the housing actuator assembly may be provided attached to the sheath 52 as long as the lumen 60 may be accessed. In a further alternative, the housing 54 may be provided separately from the sheath 62 with the clip 10 preloaded therein. For example, the housing 54 may be provided on an elongate member, such as a tubular or U-shaped sleeve (not shown), that may be advanced over and coupled to the sheath 64 at any time before deployment of the clip 10. The housing actuator may be coupled to the sleeve and/or may be attachable to the sleeve.

The sheath 52 may be advanced over a guidewire or other rail (not shown) previously positioned through the passage 92 into the blood vessel 90 using a conventional procedure. Preferably, the blood vessel 90 is a peripheral vessel, such as a femoral, radial, or carotid artery, although other body lumens may be accessed using the sheath 52, as will be appreciated by those skilled in the art.

The passage 92, and consequently the sheath 52, may be oriented at a substantially acute angle "alpha" with respect to the vessel 90, thereby facilitating introduction of devices through the lumen 60 of the sheath 52 into the vessel 90 with minimal risk of damage to the vessel 90. One or more devices, such as a guide wire, a catheter, and the like (not shown), may be inserted through the sheath 52 and advanced to a desired location within the patient's body. For example, the devices may be used to perform a therapeutic or diagnostic procedure, such as angioplasty, atherectomy, stent implantation, and the like, within the patient's vasculature.

After the procedure is complete, the device(s) may be removed from the sheath 52. The sheath 52 may be manipulated to position the distal end 64 with respect to the opening 92, e.g., to ensure that the housing 54 is advanced to properly deploy the clip 10 in the wall 98 of the vessel 90. Bleed back or mechanical locators may be used to facilitate this positioning.

As shown in FIG. 10B, with the sheath 52 properly positioned, the housing 54 may be actuated, for example, to advance the housing 54 distally into the passage 92 to deliver the clip 10. Preferably, movement of the housing 54 with respect to the distal end 64 of the sheath 52 is limited, e.g., by the actuator assembly. Thus, the housing 54 may only be advanced a fixed distance such that the clip 10 substantially engages the wall 98 of the blood vessel 90, e.g., until the tines 18 penetrate but do not pass completely through the wall 98. Once the clip 10 is successfully deployed within the passage 92, i.e., into the wall 98 of the vessel 90, the apparatus 50 may be withdrawn from the passage 92.

In addition, as the clip 10 is deployed from the housing 54, the clip 10 may expand radially to an enlarged diameter (not shown), for example, if the clip 10 includes expandable elements (not shown), such as those described above. Thus, the clip 10 may be compressed into the housing 54, e.g., thereby allowing a smaller profile housing 54 to be used. The clip 10 may be expanded upon deployment to engage a larger area of tissue adjacent the opening in the wall 98 of the vessel 90.

Figures 10C, 10D:
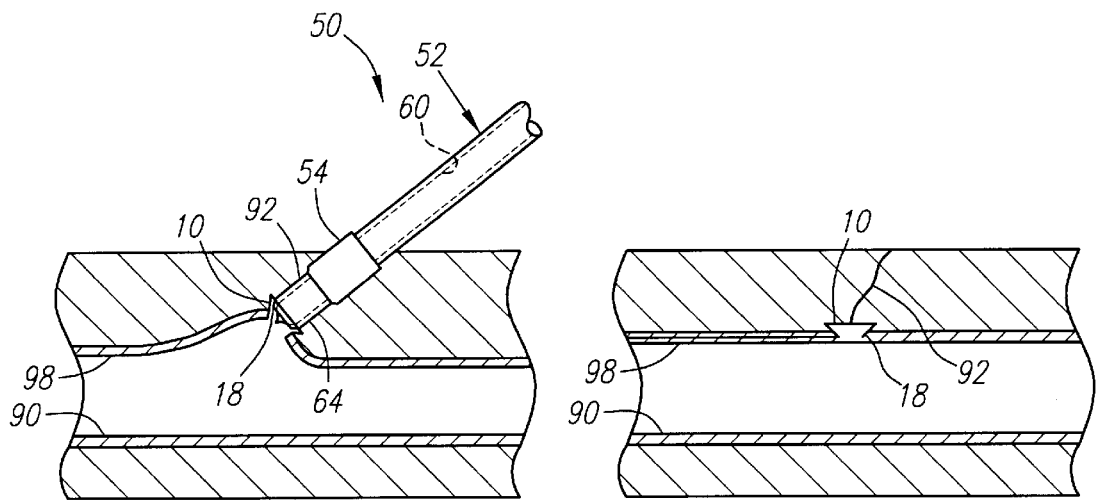

As shown in FIG. 10C, as the distal end 64 of the sheath 52 is withdrawn proximally from around the clip 10, the tines 18 of the clip 10 are free to return towards the planar configuration. Thus, the tines 18 begin automatically to move from a substantially axial configuration to a less transverse configuration. Because the tines 18 are engaged to the tissue, however, they may not return completely to the planar configuration. Because of the bias to the planar configuration, however, the tines 18 automatically pull the tissue together, thereby closing and/or sealing the passage 92, as shown in FIG. 10D. In addition, if desired a sealant or other material may be introduced into the passage 92 in conjunction with or separate from delivery of the clip 10 to further seal the passage 92, as is known to those skilled in the art.

Figure 11A:
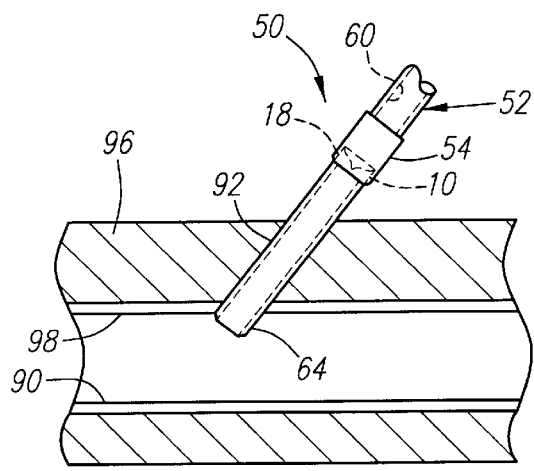
FIGS. 11A–11D are cross-sectional views of a blood vessel, showing another method for delivering a closure device into a passage communicating with the vessel such that the closure device engages extra-vascular tissue proximal to the vessel wall.
Figure 11B:
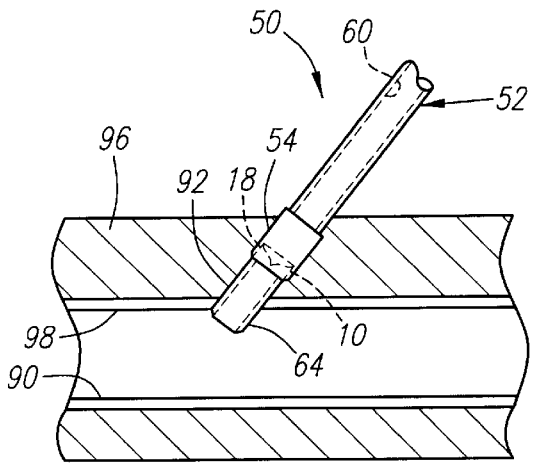
Figure 11C:
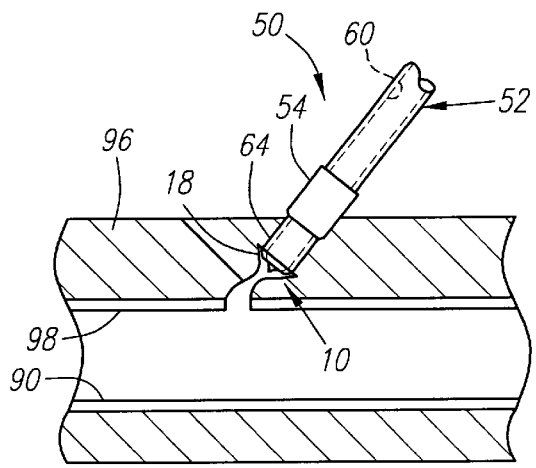
Figure 11D:
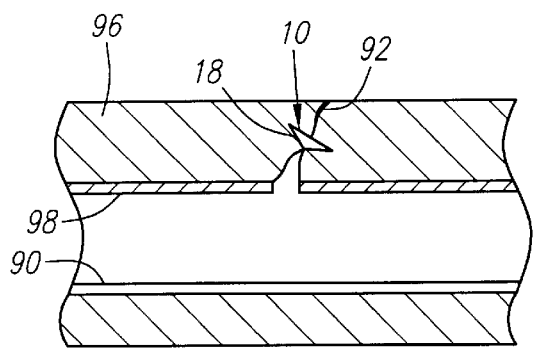

Turning to FIGS. 11A–11C, another method is shown in which the apparatus 50 may be used to deliver a clip 10, e.g., to engage intervening tissue 96 to close and/or seal an incision, puncture, or other passage 92 that extends from a patient's skin 94 through the intervening tissue 96, to a wall 98 of the vessel 90. As shown in FIG. 11A, the sheath 52 may be inserted or otherwise positioned within the blood vessel 90, i.e., through the passage 92. One or more devices (not shown) may be inserted through the sheath 52 to perform a procedure within the patient's body. After the procedure is complete, the device(s) may be removed from the sheath 52, and the sheath 52 may be manipulated to position the distal end 64 within the passage 92.

Turning to FIG. 11B, with the sheath 52 properly positioned, the housing 54 may be actuated, for example, to advance the housing 54 distally into the passage 92 to deliver the clip 10 to a location between the patient's skin 94 and the vessel wall 98. The clip 10 may be deployed from the housing 54, thereby substantially engaging fascia or other intervening tissue 96 with the tines 18. Once the clip 10 is successfully deployed within the passage 92, the apparatus 50 may be withdrawn from the passage 92.

As shown in FIG. 11C, as the distal end 64 of the sheath 52 is withdrawn proximally from around the clip 10, the tines 18 of the clip 10 are free to return towards the planar configuration. Because of the bias to the planar configuration, the tines 18 automatically pull the tissue together, thereby closing and/or sealing the passage 92, as shown in FIG. 10D.

Figure 12:
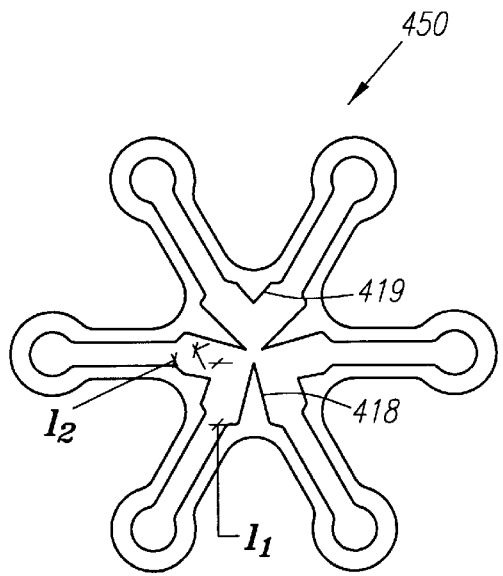
FIG. 12 is a top view of an alternative embodiment of a clip, in accordance with the present invention.

In a further alternative, shown in FIG. 12, a clip 450 may be provided that includes a first set of tines 418 having a first length $l_1$, and a second set of tines 419 having a second length $l_2$ substantially shorter than the first length $l_1$. During use, similar to one of the methods described above, the clip 450 may be deployed such that the first set of tines 418 penetrate into and/or engage the wall of a blood vessel or other body lumen (not shown), while the second set of tines 418 engage extra-vascular tissue, i.e., tissue between the vessel wall and the patient's skin. Thus, the clip 450 may simultaneously close both the opening in the vessel wall and the passage through the intervening tissue.

Figure 13:
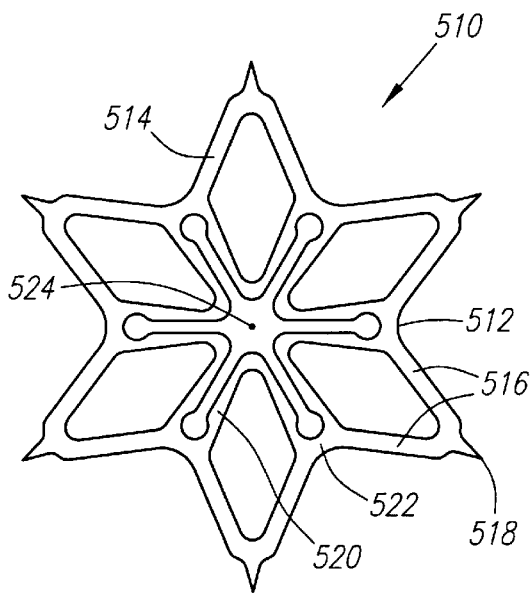
FIGS. 13–15 are top views of additional embodiments of a clip, in accordance with the present invention.

Turning to FIG. 13, another preferred embodiment of a clip 510 is shown for engaging tissue, in accordance with the present invention. The clip 510 includes a peripheral body 512 and a plurality of tissue engaging portions 514. Each tissue engaging portion 514 includes a pair of legs 516 terminating in a tine 518 configured for penetrating or otherwise engaging tissue. The tissue engaging portions 514 are disposed substantially symmetrically about a central axis 524. The body 512 also preferably includes a plurality of expandable cells 520 that are connected by hinged regions 522 that also connect adjacent tissue engaging portions 514, the cells 520 behaving similar to the embodiments described above.

In a preferred embodiment, the body 512 and tissue engaging portions 514 are integrally formed from a single sheet of material, such as a Nitinol, similar to the embodiments described above. The clip 510 is shown in a relaxed state with the tissue engaging portions 514 disposed radially outward in a substantially planar configuration. Similar to the previous embodiments, the tissue engaging portions 514 may be deflected such that they extend from the body 512 substantially transversely with respect the plane defined by the sheet (similar to FIG. 1B).

Preferably, the tissue engaging portions 514 are biased from the transverse configuration away from one another, i.e., towards the planar configuration. Thus, with the tissue engaging portions 514 in the transverse configuration, the tines 518 may be engaged with tissue. When the clip 510 is released, e.g., from within a delivery device, the tissue engage portions 514 may attempt to return to the planar configuration, thereby securing the tissue with respect to the clip 510.

In addition, the clip 510 may include expandable cells 520 that are expandable from a compressed state to an expanded state (similar to FIG. 1C), similar to the previous embodiments. Preferably, the expandable cells 520 are biased to the expanded state, but may be compressed to the compressed state, e.g., by constraining the clip 510. Alternatively, any of the clips described herein may be biased to the compressed state but may be expanded to the expanded state, e.g., by constraining the clip over a sheath or other elongate member.

Figure 14:
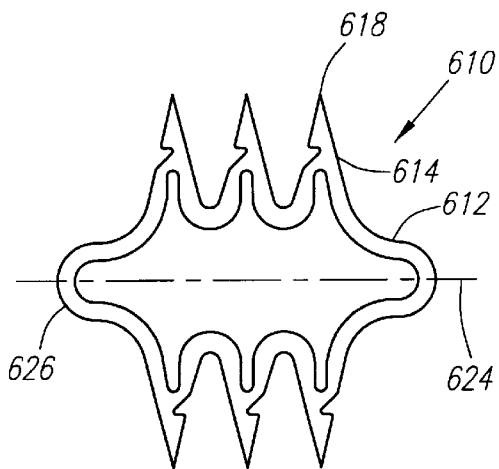

Turning to FIG. 14, yet another preferred embodiment of a clip 610 is shown that includes a peripheral body 612 and a plurality of tissue engaging portions 614 terminating in tines 618. The clip 610 may be formed from a single sheet of material, such as Nitinol or may be formed from a wire, rod or tube (not shown), similar to the embodiments described above. The tissue engaging regions 614 are disposed in opposing sets oriented away from one another along an axis of symmetry 624, defining a substantially planar configuration.

The tissue engaging portions 614 may be directed substantially transversely with respect to a plane defined by the planar configuration, for example, by loading the clip 614 into a housing or lumen of a delivery device (not shown). The tissue engaging portions 614 are preferably biased to move away from one another, i.e., towards the planar configuration. In an alternative embodiment, the looped regions 626 or other regions of the body 612 may include expandable elements (not shown), e.g., having a zig-zag shape, a diamond shape, and the like.

Figure 15:
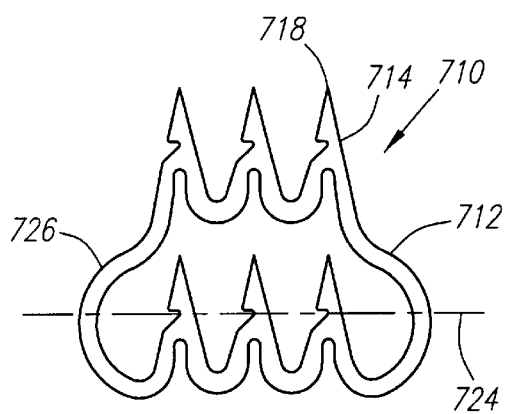

Turning to FIG. 15, still another preferred embodiment of a clip 710 is shown that includes a peripheral body 712 and a plurality of tissue engaging portions 714 terminating in tines 718. The clip 610 is similar to the previous embodiment, except that the tissue engaging regions 714 are disposed in opposing sets along an axis of symmetry 724, but are oriented in a common direction. The tissue engaging portions 714 may be directed substantially transversely with respect to a plane defined by the planar configuration. The tissue engaging portions 714 are preferably biased to return towards the planar configuration shown. In an alternative embodiment, the looped regions 726 or other regions of the body 712 may include expandable elements (not shown), e.g., having a zig-zag shape, a diamond shape, and the like, similar to the previous embodiments.

The clip 710 may be constrained on a delivery apparatus (not shown), similar to that described above, such that the tissue engaging portions 714 are all directed substantially transversely, preferably distally, to facilitate their engagement into tissue during deployment, as will be appreciated by those skilled in the art. Unlike previous embodiments, which may close tissue around an opening, this embodiment may be useful when it is desired to maintain the relative position of tissue being engaged by thew clip 710.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A device for engaging tissue, comprising:
   a generally annular-shaped body;
   an expandable element disposed along a periphery of the annular-shaped body, the expandable element being compressible to a compressed state to facilitate delivery and being biased to expand from the compressible state to an expandable state for increasing a peripheral dimension of the annular-shaped body upon deployment; and
   a plurality of tissue engaging portions extending from the annular-shaped body, wherein the tissue engaging portions are biased towards a substantially planar configuration and opposing tissue engaging portions are biased towards one another such that they will have the substantially planar configuration when they are not deflected.

2. The device of claim 1, wherein the expandable element comprises a zig-zag element.

3. The device of claim 1, wherein the expandable element comprises an arcuate element.

4. The device of claim 1, wherein the tissue engaging potions are initially formed in the substantially planar configuration, the tissue engaging portions being deflected substantially transversely with respect to said planar configuration to define a substantially transverse configuration.

5. A device for engaging tissue, comprising:
   a generally annular-shaped body having a plurality of tissue engaging portions and a plurality of hinged regions connecting adjacent tissue engaging portions, said tissue engaging portions extending from the annular-shaped body and defining a plane when said tissue engaging portions are not deflected from said plane, said tissue engaging portions being deflected from said plane and extending substantially transversely with respect to the plane, the tissue engaging portions being biased towards a substantially planar configuration lying in the plane, wherein opposing tissue engaging portions are biased towards one another such that they will have the substantially planar configuration when they are not deflected.

6. The device of claim 5, wherein the tissue engaging portions comprise barbs for penetrating tissue.

7. The device of claim 5, wherein the tissue engaging portions comprise a first set of tines having a first length and a second set of tines having a second length shorter than the first length.

8. The device of claim 7, wherein the first and second seta of tines are disposed symmetrically alternatively about a central axis and such that each of the first set of tines is located adjacent to two of the second set of tines.

9. The device of claim 8, comprising an equal number of the first set of tines and the second set of tines.

10. The device of claim 5, wherein the tissue engaging portions and the annular-shaped body are formed from a sheet of material.

11. The device of claim 10, wherein the sheet of material comprises a superelastic alloy.

12. The device of claim 10, wherein the tissue engaging portions are formed from the sheet of material in the substantially planar configuration, the tissue engaging portions being deflectable substantially transversely with respect to the plane to define a substantially transverse configuration.

13. The device of claim 5, wherein the tissue engaging portions are disposed symmetrically about a central axis.

14. The device of claim 5, wherein opposing tissue engaging portions are oriented towards one another in the substantially planar configuration.

15. The device of claim 5, further comprising a plurality of arms, wherein each arm connects one of the hinged regions to the adjacent tissue engaging portion.

16. The device of claim 15, wherein the tissue engaging portions are disposed symmetrically about a central axis, and each of the plurality of arms extends from the hinged region to the adjacent tissue engaging portion in a radially inward direction at least partially towards the center axis.

* * * * *